United States Patent
Breuel et al.

(10) Patent No.: US 11,185,621 B2
(45) Date of Patent: Nov. 30, 2021

(54) APPARATUS FOR CARRYING OUT AN EXTRACORPOREAL BLOOD TREATMENT

(71) Applicant: FRESENIUS MEDICAL CARE DEUTSCHLAND GMBH, Bad Homburg (DE)

(72) Inventors: Lars Breuel, Witzleben (DE); Gerhard Mager, Bad Homburg (DE); Georg Verch, Wiesbaden (DE); Juergen Klewinghaus, Oberursel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 610 days.

(21) Appl. No.: 15/998,643

(22) PCT Filed: Feb. 9, 2017

(86) PCT No.: PCT/EP2017/000184
§ 371 (c)(1),
(2) Date: Aug. 16, 2018

(87) PCT Pub. No.: WO2017/140416
PCT Pub. Date: Aug. 24, 2017

(65) Prior Publication Data
US 2020/0330673 A1    Oct. 22, 2020

(30) Foreign Application Priority Data
Feb. 16, 2016    (DE) .................... 10 2016 001 765.1

(51) Int. Cl.
*A61M 1/34*     (2006.01)
*A61M 1/36*     (2006.01)
(Continued)

(52) U.S. Cl.
CPC ........ *A61M 1/3437* (2014.02); *A61M 1/3424* (2014.02); *A61M 1/3496* (2013.01);
(Continued)

(58) Field of Classification Search
CPC .............. A61M 1/3424; A61M 1/3437; A61M 1/3496; A61M 1/3646; A61M 1/369;
(Continued)

(56) References Cited

U.S. PATENT DOCUMENTS

| | | |
|---|---|---|
| 6,824,524 B1 | 11/2004 | Favre |
| 2008/0243045 A1 | 10/2008 | Pasqualini |
| 2009/0124963 A1* | 5/2009 | Hogard .................. A61M 1/14 604/30 |

FOREIGN PATENT DOCUMENTS

| | | |
|---|---|---|
| CA | 2704411 | 5/2009 |
| DE | 102006042120 | 4/2008 |

(Continued)

*Primary Examiner* — John Kim
(74) *Attorney, Agent, or Firm* — Jacobson Holman PLLC

(57) ABSTRACT

The invention relates to an apparatus for carrying out an extracorporeal blood treatment in which a substitution fluid is administered to the patient, wherein the apparatus comprises an extracorporeal blood circuit and a substitution line opening into the extracorporeal blood circuit, wherein the substitution line has at least one heating container, and wherein a pump is arranged in the substitution line downstream of the heating container or containers for the conveying of substitution fluid into the extracorporeal blood circuit.

3 Claims, 5 Drawing Sheets

(51) Int. Cl.
*A61M 5/44* (2006.01)
*A61M 60/892* (2021.01)

(52) U.S. Cl.
CPC .......... *A61M 1/369* (2013.01); *A61M 1/3646* (2014.02); *A61M 5/445* (2013.01); *A61M 60/892* (2021.01); *A61M 2205/3386* (2013.01); *A61M 2205/3389* (2013.01); *A61M 2205/36* (2013.01); *A61M 2205/75* (2013.01); *A61M 2205/7518* (2013.01)

(58) Field of Classification Search
CPC ................ A61M 60/892; A61M 5/445; A61M 2205/3386; A61M 2205/3389; A61M 2205/36; A61M 2205/75; A61M 2205/7518
See application file for complete search history.

(56) References Cited

FOREIGN PATENT DOCUMENTS

| | | |
|---|---|---|
| DE | 102008026916 | 12/2009 |
| DE | 102009008346 | 8/2010 |
| DE | 102009037917 | 2/2011 |
| DE | 102010032179 | 1/2012 |
| DE | 102014008546 | 12/2015 |
| DE | 102014108444 | 12/2015 |
| EP | 0763367 | 3/1997 |
| EP | 2291207 | 3/2011 |
| EP | 2324871 | 5/2011 |
| WO | WO 02/062454 | 8/2002 |
| WO | WO 2009/147478 | 12/2009 |

\* cited by examiner

APPARATUS FOR CARRYING OUT AN EXTRACORPOREAL BLOOD TREATMENT

The invention relates to an apparatus for carrying out an extracorporeal blood treatment in which a substitution fluid is administered to the patient.

In plasmapheresis, plasma is removed from the blood of a patient using a filter arranged in an extracorporeal blood circuit. The method is used, for example, for the treatment of some autoimmune diseases. In a variant of the method which is called plasma exchange, the removed plasma is discarded and a substitution fluid is introduced into the extracorporeal blood circuit.

The invention is, however, not restricted to plasmapheresis, but can rather generally be applied to devices for extracorporeal blood treatment in which a non-endogenous substitution fluid is supplied to the patient.

At least one heating pouch in which the substitution fluid is heated to body temperature is usually arranged in the substitution line. At the end of the treatment, the substitution fluid contained in the heating pouches is infused in accordance with the prior art into the extracorporeal blood circuit by displacement fluid using a displacement. In this respect, a mixing of the two liquids can take place in the substitution line and in particular in the heating pouches, which prevents a complete reinfusion of the substitution solution. Provided that plasma is used as the substitution fluid and that a physiological NaCl solution is used as the displacement fluid, the greater density of the plasma (1.028 over 1.0046 g/ml) in the heating pouches normally filled from bottom to top for venting also promotes the mixing of both fluids.

It is the object of the invention to provide an apparatus of the category in which these disadvantages are avoided.

Against this background, the invention relates to an apparatus for carrying out an extracorporeal blood treatment in which substitution fluid is administered to the patient, wherein the apparatus comprises an extracorporeal blood circuit and a substitution line opening into the extracorporeal blood circuit and wherein the substitution line has at least one heating container. Provision is made in accordance with the invention that a pump for conveying substitution fluid into the extracorporeal blood circuit is arranged in the substitution line downstream of the heating container or containers.

Due to the arrangement of the pump downstream of the comparatively high-volume heating containers, the latter can be sucked empty in the end phase of the treatment after an interruption of the supply of fluid on the lead side.

In an embodiment, the heating containers are compressible. They are preferably plastic pouches. In this case, the pouch volume can reduce as the contained fluid volume reduces on the sucking empty by the pump.

In an embodiment, a clamp which inhibits the flow of substitution solution in the closed state is arranged upstream of the heating container or containers in the substitution line. A possibility of interrupting the supply of fluid on the lead side is the provision of a clamp.

In an embodiment, the apparatus furthermore has a control unit which is connected to the pump, and optionally to the clamp, and which is configured such that the clamp is closed and the pump is operated in an operating mode of the apparatus. This operating mode corresponds to the end phase of the treatment when additional substitution fluid is no longer required.

An embodiment variant in this respect comprises a manual clamp which is not connected to the control unit. If the control unit is only connected to the pump, the state of the clamp can, for example, be transmitted to the control unit by the user using an interface, for example.

In an embodiment, a respective at least one interface is arranged upstream of the heating container or containers, between the heating container or containers and the pump as well as downstream of the pump, at which interface the substitution line can be separated, wherein the interfaces are so compatible with one another that the heating container(s) could alternatively also be used downstream of the pump. The configuration with the pump downstream of the container or containers does not have to correspond to the configuration which is present in the normal phase of the treatment. It is equally conceivable to change the configuration before initiating the end phase of the treatment and in so doing in particular to change the position of the pump relative to the container or containers. If a respective interface at which the substitution line can be separated is arranged upstream and downstream of the pump, the containers can selectively be integrated into the substitution line upstream or downstream of the pump. It is thus conceivable that the apparatus adopts a normal configuration during the treatment in which the pump is arranged upstream of the containers and adopts the configuration with the downstream pump in the end phase of the treatment in which the pump is arranged downstream of the containers. The conversion can in this respect take place by machine or manually.

In an embodiment, a further pump is arranged upstream of the heating container or containers in the substitution line for the conveying of substitution fluid into the extracorporeal blood circuit. A possibility of interrupting the supply of fluid on the lead side is also given by the provision of a further pump which is arranged upstream of the container or containers and which is taken out of operation during the end phase of the treatment and develops a blocking effect in this state. At the same time, this upstream pump can naturally also serve the fluid conveying, for example during the normal phase of the treatment.

In an embodiment, the substitution line has a bypass line in the region of the downstream pump, in which bypass line a check valve is preferably arranged which allows a flow only in the direction of the extracorporeal blood circuit. If provision is made not to operate the downstream pump during the normal phase of the treatment and instead to use the upstream pump, a bypass line has to be present so that the substitution fluid can flow past the idling downstream pump which in this respect develops a blocking effect. The check valve serves the purpose of avoiding a short-circuit by the bypass in the end phase of the treatment when the upstream pump is idling and the downstream pump is operated to suck the heating container or containers empty.

In an embodiment, the apparatus furthermore has a control unit which is connected to the pumps and which is configured such that the upstream pump is stopped and the downstream pump is operated in an operating mode of the apparatus. This operating mode corresponds to the end phase of the treatment when additional substitution fluid is no longer required.

Against the initially named background, the invention furthermore relates to an apparatus for carrying out an extracorporeal blood treatment in which a substitution fluid is administered to the patient, wherein the apparatus comprises an extracorporeal blood circuit and a substitution line opening into the extracorporeal blood circuit, and wherein the substitution line has at least one pump for conveying substitution fluid into the extracorporeal blood circuit and at least one heating container. Provision is made in accordance with the invention in this respect that the upstream end of the substitution line is provided with a sterile filter and projects into a gas-filled space. The upstream end of the substitution line preferably simply projects into the environmental air which is sterilized at the sterile filter before entry into the substitution line.

This corresponds to the configuration of the apparatus of the category during the end phase of the treatment in which the remainder of substitution fluid present in the heating containers should be infused into the extracorporeal blood circuit in which, however, no new substitution fluid and no new displacement fluid should run into the substitution line, but rather only gas or air.

In an embodiment of this invention variant, the pump is arranged downstream of the heating containers. In another embodiment of this invention variant, the heating containers are arranged such that they are flowed through from top to bottom. These embodiments ensure an improved function of the system.

In an embodiment, the apparatus furthermore has a control unit and, optionally, a sensor for measuring the conveying quantity of the pump, wherein the control unit is connected to the pump and, optionally, to the quantity sensor and is configured such that the conveying quantity of the pump is measured and the pump is switched off on reaching a specific total conveying quantity in an operating phase of the apparatus.

In an embodiment, the extracorporeal blood circuit has a drop chamber downstream of the opening point of the substitution line and the apparatus furthermore has a control unit and a sensor for measuring the filling level of the drop chamber, wherein the control unit is connected to the pump and to the filling level sensor and is configured such that the filling level of the drop chamber is measured and the pump is switched off on reaching a specific minimum filling level in an operating phase.

These operating phases each correspond to the end phase of the treatment when additional substitution fluid is no longer required.

The apparatus in accordance with the invention preferably serves the carrying out of a plasmapheresis treatment. The pump or pumps is/are preferably peristaltic pumps.

Against the initially named background, a method is contemplated for carrying out an extracorporeal blood treatment and preferably a plasmapheresis treatment in which the supply of fluid is interrupted upstream of the substitution line in an end phase of the treatment and the heating pouch or pouches in which substitution fluid is still present is/are sucked empty by a pump which is arranged downstream of these pouches and which conveys the substitution fluid in the direction of the extracorporeal blood circuit. This method preferably takes place in the end phase of the treatment using an apparatus which has the configuration for carrying out an extracorporeal blood treatment in which a substitution fluid is administered to the patient, wherein the apparatus comprises an extracorporeal blood circuit (1) and a substitution line (25) opening into the extracorporeal circuit blood circuit (1), and wherein the substitution line (25) has at least one heating container (28), characterized in that a pump (27, 31) is arranged downstream of the heating container or containers (28) in the substitution line (25) for conveying substitution fluid into the extracorporeal blood circuit (1).

A method for carrying out an extracorporeal blood treatment, and preferably a plasmapheresis treatment, is furthermore contemplated in which gas, and in particular air, is used in an end phase of the treatment to displace the substitution fluid contained in the heating pouch or pouches of the substitution line in the direction of the extracorporeal blood circuit. This method preferably takes place in the end phase of the treatment using an apparatus which has the configuration for carrying out an extracorporeal blood treatment in which a substitution fluid is administered to the patient, wherein the apparatus comprises an extracorporeal blood circuit (1) and a substitution line (25) opening into the extracorporeal blood circuit, and wherein the substitution line (25) has at least one pump (27) for conveying substitution fluid into the extracorporeal blood circuit (1) and at least one heating container (28), characterized in that the upstream end of the substitution line (25) is provided with a sterile filter (20) and projects into a gas-filled space.

It is common to all apparatus in accordance with the invention and to all contemplated methods that no displacement of the substitution fluid takes place with a displacement fluid such as physiological saline solution. It is rather the case that either the substitution line is interrupted upstream of the heating pouches and the heating containers are sucked empty or a displacement with gas, and in particular air, takes place.

BRIEF DESCRIPTION OF THE DRAWINGS

Further details and advantages of the invention result from the embodiments explained in the following with reference to the Figures. There are shown in the Figures:

FIG. 1 shows an apparatus of the category during the normal phase of the treatment in which fresh substitution fluid is continuously obtained from a reservoir and is administered to the patient.

Figure 1:
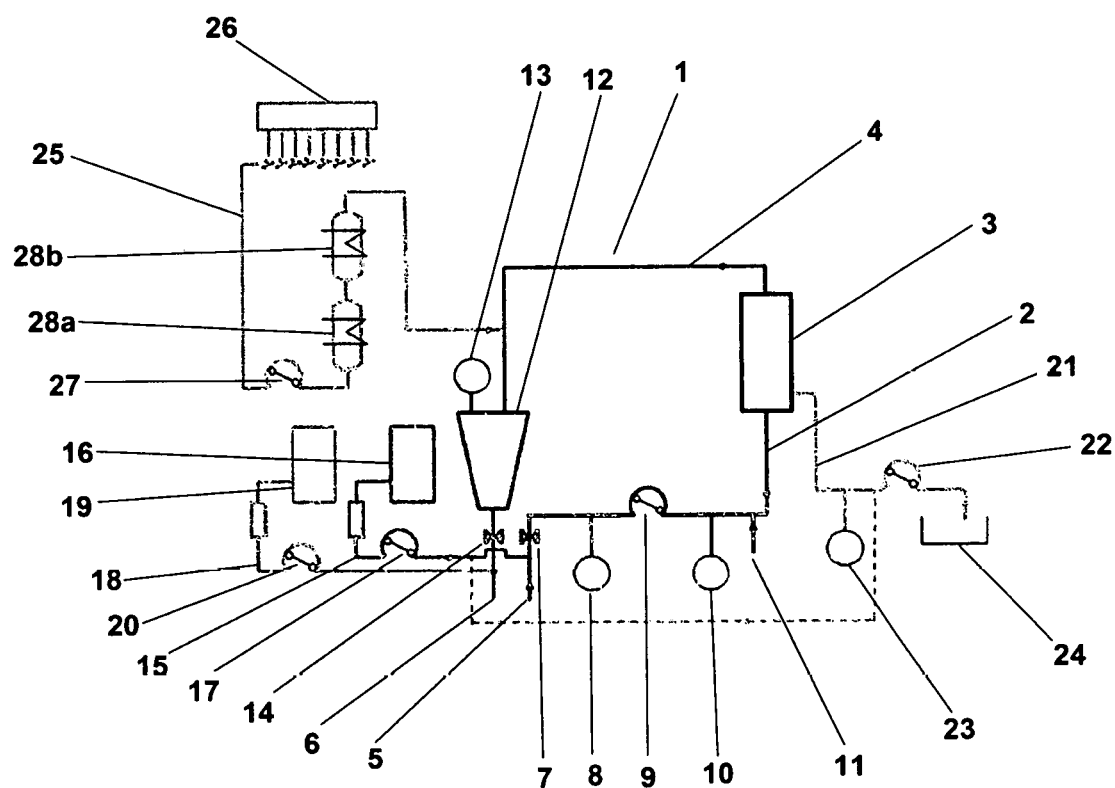
FIG. 1: a flow diagram of an apparatus for plasma exchange during the normal phase of the treatment.

The extracorporeal blood circuit of the apparatus is marked by the reference numeral 1. It comprises an arterial line 2, a plasma filter 3 and a venous line 4. An arterial port 5 is arranged at the lead side of the arterial line 2 and a venous port 6 is arranged at the return side of the venous line 4. These ports 5 and 6, which are needles, for example, serve the connection of the apparatus to a patient.

An arterial clamp 7, a pressure sensor 8 for measuring the arterial pressure, a blood pump 9, a further pressure sensor 10 for measuring the pump pressure, and a line 11 for supplying an anticoagulant such as heparin are arranged staggered in the direction of flow in the arterial line 2.

A drop chamber 12, a pressure sensor 13 for measuring the venous pressure and a venous clamp 14 are located in the venous line 4.

In addition, a metering system 15 for citrate is connected to the arterial line 2 between the arterial port 5 and the arterial clamp 7, said metering system comprising a citrate reservoir 16 and a citrate pump 17. A metering system 18 for calcium ions which comprises a calcium ion reservoir 19 and a calcium pump 20 is connected to the venous line 4 between the venous clamp 14 and the venous port 6.

The plasma filter 3 comprises a semipermeable membrane which separates the extracorporeal blood circuit 1 from a drainage system 21 for plasma separated from the blood. The drainage system 21 comprises a filtration pump 22, a pressure sensor 23 for measuring the filtration pressure and a drain 24 for collecting or disposing of the separated plasma.

The apparatus furthermore comprises a substitution line 25 which opens into the venous line 4 of the extracorporeal blood circuit 1 upstream of the drop chamber 12. A reservoir 26 for substitution fluid is arranged at the lead side of the substitution line 25. A substitution pump 27 which serves the conveying of substitution fluid from the reservoir 26 into the venous line 4 is furthermore arranged in the substitution line 25. The substitution line 25 furthermore comprises heating pouches 28a and 28b which comprise a heat exchanger and which serve to raise the temperature of the substitution fluid to body temperature.

Figure 2:
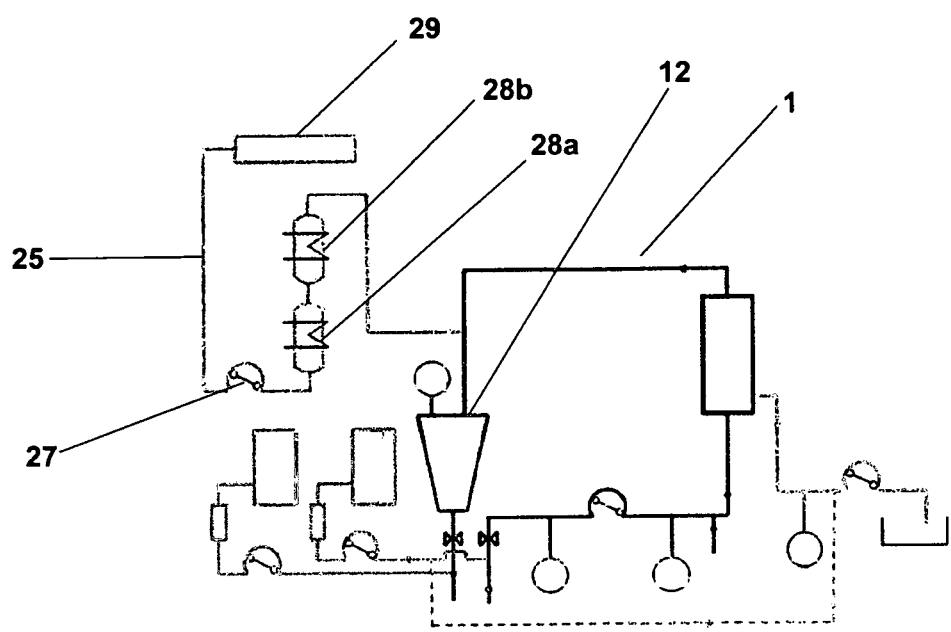
FIG. 2: a flow diagram of an apparatus for plasma exchange during the end phase of the treatment, with a displacement of the substitution fluid taking place with a displacement fluid.

FIG. 2 shows the same apparatus during the end phase of the treatment in which fresh substitution fluid is no longer obtained and administered to the patient. Instead, the remainder of the substitution fluid still located in the substitution line 25, and in particular in the heating pouches 28a and 28b, should be conveyed into the extracorporeal blood circuit 1 by displacement with a displacement fluid. For this purpose, the reservoir 26 for substitution fluid is replaced with a reservoir 29 for a displacement fluid in the end phase of the treatment. The substitution pump 27 then conveys displacement fluid out of the reservoir 29 for so long until the total volume of the substitution line 25 and of the heating pouches 28a and 28b has been flushed empty. The determination of the conveyed volume can take place, for example, with reference to a flow sensor not shown in the Figures. In this method, however, the problems named in the introductory part of the description result of a mixing and incomplete displacement.

Figure 3:
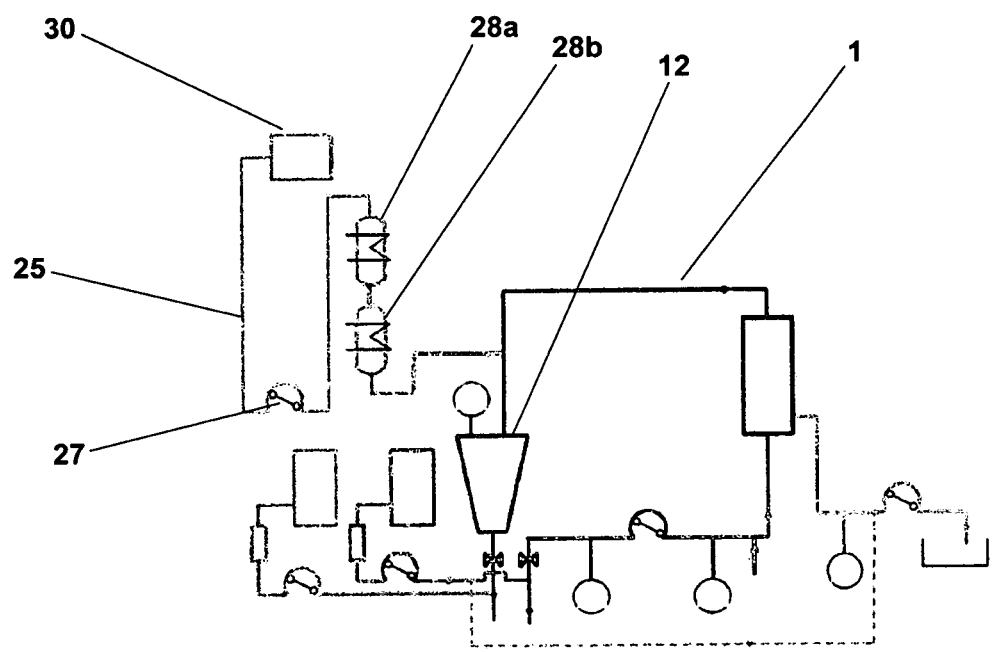
FIG. 3: a flow diagram of an apparatus in accordance with the invention for plasma exchange during the end phase of the treatment, with a displacement of the substitution fluid taking place with air.

An apparatus configured in accordance with the invention during the end phase of the treatment is shown in FIG. 3.

Instead of the physiological NaCl solution (cf. reservoir 29 of FIG. 2), no fluid reservoir, but rather only a sterile filter 30 is now connect to the hose system. Since the heating pouches 28a and 28b are flowed through from bottom to top, they should be removed from the heating and turned over in this solution (which is not shown in the Figure), for example suspended upside down at an infusion stand.

Air is subsequently conveyed for so long by the substitution pump 27 until the plasma has been completely reinfused in the heating pouches 28a and 28b and in the hose system 25 up to the venous drop chamber 12. The reinfusion is easy to monitor by staff since the boundary layer between air and plasma is easily visible.

No danger arises from this since any air conveyed is intercepted in the venous drop chamber 12 and, with large quantities, could be reliably recognized there or in a subsequent detector not shown in the Figure. The reinfusion could be automated in that the end of the reinfusion is determined by the volume to be conveyed by the substitution pump 27 or by the drop of the level in the venous drop chamber 12.

Advantages of this variant comprise an almost complete plasma reinfusion, with the costs for the physiological NaCl reinfusion solution being dispensed with.

Figure 4:
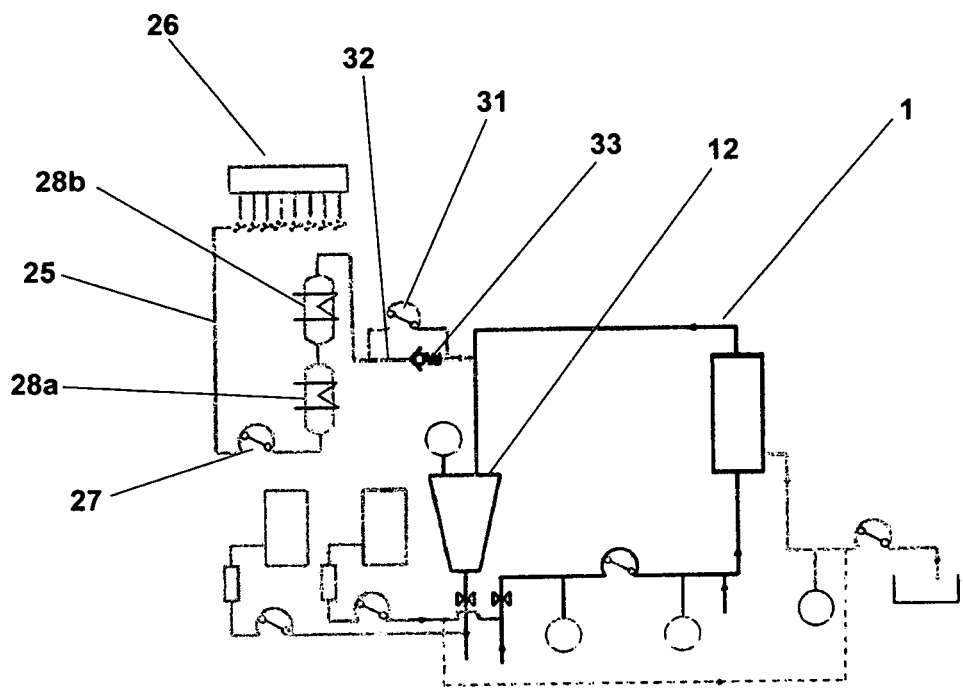
FIG. 4: a flow diagram of a variant of an apparatus in accordance with the invention for plasma exchange, with the heating containers being sucked empty during the end phase of the treatment.

A further variant in accordance with the invention of an apparatus of the category is shown during the end phase of the treatment in FIG. 4.

The reinfusion of the plasma contained in the heating pouches 28a and 28b and in the line 25 takes place here by an additional pump 31 which is connected in parallel with a bypass line 32 in the substitution line 25 between the heating pouches 28a and 28b and the extracorporeal blood circuit 1. So that the heating pouches 28a and 28b can be sucked empty by this additional pump 31, a check valve 33 is arranged in the bypass line.

During the reinfusion (end phase of the treatment), the substitution pump 27 is stopped and the additional pump 31 conveys the plasma located in the heating pouches 28a and 28b to the blood hose 1. The reinfusion can be automated in that the end of the reinfusion is determined by the volume to be conveyed by the additional pump 31.

In a variant, a check valve can be used which is anyway present at the plasma infusion point in some devices by connecting the substitution line 25 to the additional pump 31 at the venous bubble trap 12.

Advantages of this solution comprise an almost complete plasma reinfusion, with the costs for the physiological NaCl reinfusion solution being dispensed with. An automated handling of the reinfusion is furthermore possible. There is no risk for the patient for the reasons already named in connection with the discussion of FIG. 3.

Figure 5:
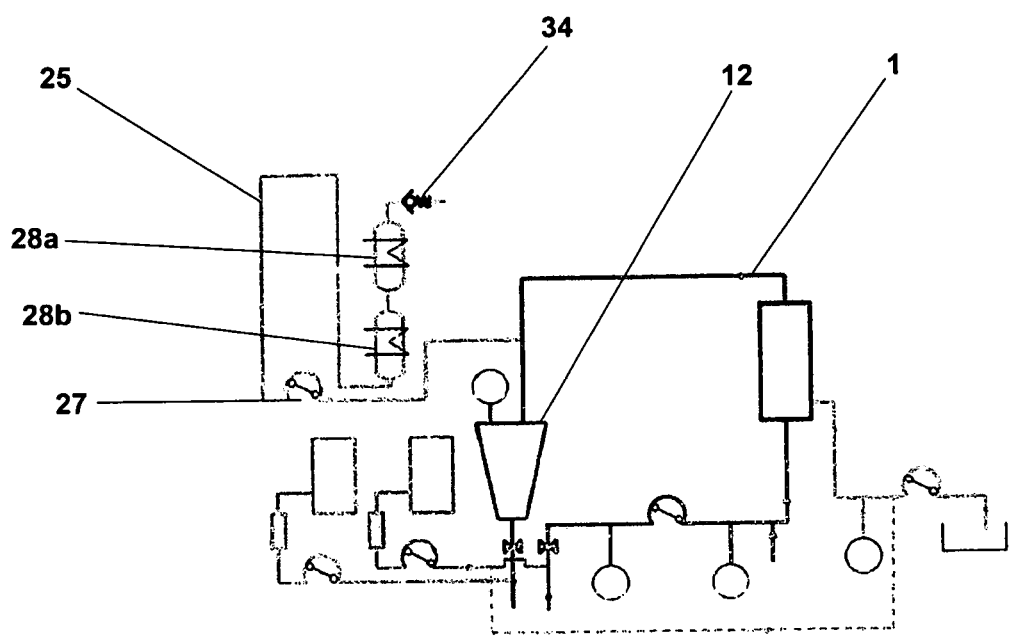
FIG. 5: a flow diagram of a further variant of an apparatus in accordance with the invention for plasma exchange, with the heating containers being sucked empty during the end phase of the treatment.

A further variant in accordance with the invention of an apparatus of the category is shown during the end phase of the treatment in FIG. 5.

In accordance with this variant, a reclamping of the heating pouches 28a and 28b is provided for an almost complete plasma reinfusion. Before the start of the end phase of the treatment, the heating pouches 28a and 28b are removed from the substitution line 25 and are connected upstream of the substitution pump 27. The other side of the heating pouches 28a and 28b can be closed, for example using a clamp 34. The substitution line 25 is closed again at the point at which the heating pouches 28a and 28b were. The plasma located in the heating pouches 28a and 28b can now be conveyed by the substitution pump 27 to the extracorporeal blood circuit 1.

Advantages of this variant comprise an almost complete plasma reinfusion, with the costs for a physiological NaCl reinfusion solution being dispensed with.

A further variant in accordance with the invention will likewise be discussed with reference to FIG. 5. In accordance with this variant, a reinfusion can take place by closing the connector line to the reservoir 26 (shown in FIG. 1).

This solution requires the constant reversal of the arrangement of heating pouches 28a and 28b in relation to the substitution pump 27, that is the arrangement of the substitution pump 27 downstream of the heating pouches 28a and 28b, as is shown in FIG. 5. In this variant, the plasma can first be preheated in the heating pouches 28a and 28b during the normal phase of the treatment and can then be conveyed by substitution pump 27 into the extracorporeal blood circuit 1.

If the heating pouches 28a and 28b are upstream of the substitution pump 27, the access to the reservoir 26 can, for example, be closed manually for the reinfusion. This is sufficient to empty the heating pouches 28a and 28b using the substitution pump 27 without an additional pump having to be provided. The requirement is a possibility to close the access to the reservoir 26 manually or in an automated manner by a machine apparatus such as a clamp 34. After the closing, a predefined volume can be conveyed by the pump 3 which results from the calculated filling volume of the heating pouches 28*a* and 28*b*.

Advantages of this variant comprise an almost complete plasma reinfusion, a saving of the costs for the physiological NaCl reinfusion solution and no costs for additional hose couplings or other additional parts.

It is possible in each of the variants in accordance with the invention to configure the control unit of the apparatus such that plasma should continue to be obtained via the plasma filter 3 (zero balance) during the end phase of the treatment or whether this obtaining should stop (bolus administration).

What is claimed is:

1. An apparatus for carrying out an extracorporeal blood treatment in which a substitution fluid is administered to the patient, wherein the apparatus comprises
    an extracorporeal blood circuit,
    a substitution line opening into the extracorporeal circuit blood circuit (1), and wherein the substitution line has at least one heating container,
    a pump is arranged downstream of the heating container or containers in the substitution line for conveying substitution fluid into the extracorporeal blood circuit,
    a further pump arranged upstream of the heating container or containers in the substitution line for the conveying of substitution fluid into the extracorporeal blood circuit, and
    a control unit connected to the upstream and downstream pumps and configured such that the upstream pump is stopped and the downstream pump is operated in an operating mode of the apparatus.

2. An apparatus in accordance with claim 1, characterized in that a clamp which inhibits the flow of substitution fluid in the closed state is arranged upstream of the heating container or containers in the substitution line.

3. An apparatus in accordance with claim 1, characterized in that the substitution line has a bypass line in the region of the downstream pump, in which bypass line a check valve is arranged which only allows a flow in the direction of the extracorporeal blood circuit.

* * * * *